United States Patent [19]

Isa et al.

[11] 3,946,055

[45] Mar. 23, 1976

[54] METHOD OF MANUFACTURING CARBOXYLIC ACID OR ESTER THEREOF

[75] Inventors: Hiroshi Isa, Funabashi; Takeo Inagaki, Yachiyo; Yasuhiro Kiyonaga, Musashino; Masuzo Nagayama, Tokyo, all of Japan

[73] Assignee: Lion Fat & Oil Co., Ltd., Tokyo, Japan

[22] Filed: Sept. 30, 1974

[21] Appl. No.: 510,732

[30] Foreign Application Priority Data

Oct. 6, 1973 Japan................................ 48-112719

[52] U.S. Cl....... 260/410.9 R; 260/413; 260/497 R; 260/533 A
[51] Int. Cl.²...................... C11C 3/02; C11C 1/00
[58] Field of Search......... 260/410.9 R, 413, 497 R, 260/533 A

[56] References Cited
UNITED STATES PATENTS

| | | | |
|---|---|---|---|
| 2,587,858 | 3/1952 | Kenlemans...................... | 260/533 A |
| 2,880,244 | 3/1959 | Bonnell........................... | 260/533 A |
| 2,995,575 | 8/1961 | Schulz............................. | 260/497 C |
| 3,507,891 | 4/1970 | Hearne............................ | 260/410.9 R |
| 3,856,832 | 12/1974 | Ethyl............................... | 260/410.9 R |

*Primary Examiner*—Winston A. Douglas
*Assistant Examiner*—John F. Niebling
*Attorney, Agent, or Firm*—Woodhams, Blanchard and Flynn

[57] ABSTRACT

In the method of manufacturing carboxylic acids or esters thereof by reacting olefin, carbon monoxide and alcohol or water in the presence of catalyst prepared in advance by heating a cobalt compound and pyridine or at least one pyridine base selected from the group of mono-, di- and tri-alkyl (having 1~3 carbon atoms)-substituted pyridines under the pressure of carbon monoxide.

6 Claims, No Drawings

METHOD OF MANUFACTURING CARBOXYLIC ACID OR ESTER THEREOF

BACKGROUND OF THE INVENTION a. Field of the Invention

The present invention relates to a method of manufacturing carboxylic acids or esters thereof.

b. Description of the Prior Art

As the method of manufacturing carboxylic acids or esters thereof, the art of making olefin, carbon monoxide and water or alcohol react with one another in the presence of a cobalt compound has long been known. This reaction is regarded as a reaction effected by substituting water or alcohol for hydrogen in the oxo synthesis, but, as a matter of fact, in the case of effecting this reaction under the same reaction conditions as in said oxo synthesis, the speed of reaction is low and the yield of carboxylic acid or ester thereof is no more than 40% of thereabout at the highest. Accordingly, there have hitherto been made various attempts for further improvement of said reaction. For instance, Japanese patent publication No. 12854/1966 discloses a method for increasing the yield of carboxylic ester by making hydrogen and pyridine base present in the reaction zone in addition to cobalt catalyst so as to increase the speed of reaction, and the Laid-open application No. 1362/1971 teaches a method for increasing the yield of adding lactam, nitrile, amide and the like to the reaction zone. But, in either case, the progress of reaction is rather slow, so that both methods employ a high temperature and a high pressure.

However, the high-temperature/high-pressure reaction generally has various defects such that (1) the quality of the resulting fatty acid or ester thereof is not very satisfactory, (2) the cost of equipment is increased, and (3) extra safety precaution must be taken at the time of operation. Especially in the case of manufacturing a variety of products in small quantities like the manufacture of hindered esters, because it is necessary to switch the apparatus from one product to another frequently, it is unavoidable that the high-temperature/high-pressure process is disadvantageous.

Under such circumstances, the low-pressure process has drawn public attention, and as a method in this line, there is known, for instance, the method of effecting the reaction by employing rhodium catalyst or iridium catalyst under a pressure of 20~50 atmospheres (cf. the Japanese patent publication NO. 19290/1973). However, inasmuch as this method employs a costly noble metal catalyst, there is little chance for its practical application on an industrial basis from the viewpoint of the quantitative recovery of catalyst and so on.

SUMMARY OF THE INVENTION

The object of the present invention is to overcome the foregoing disadvantages of the conventional high-temperature/high-pressure reaction and to provide a method of manufacturing carboxylic acids or esters thereof at a high yield. The present invention provides a method of manufacturing carboxylic acids or esters thereof reacting olefin, carbon monoxide and alcohol or water, which method comprises preparing in advance an active ingredient of catalyst by heating a cobalt compound together with pyridine or at least one pyridine base selected from the group of mono-, di- and tri-alkyl (having 1~3 carbon atoms) — substituted pyridines under the pressure of carbon monoxide and adding the thus prepared active catalyst to the reaction zone.

Generally speaking, this reaction utilizing Reppe's reaction is usually effected under the conditions of high-temperature/high-pressure, and it has been considered that under the conditions of high-temperature/low-pressure, the catalyst would become decomposed, while under the conditions of low-temperature/low-pressure, the reaction would scarcely progress. The present inventors had conducted a series of studies on this reaction, which led to the finding that a complex of cobalt compound and pyridine is comparatively stable under a low pressure and that an active catalyst ingredient can be prepared with cobalt compound, pyridine and carbon monoxide, but the presence of alcohol or water impedes the forming of this active ingredient of catalyst remarkably. Based on this finding, the present invention comprises preparing an active catalyst ingredient in advance and accelerating the progress of the reaction under a low pressure by adding the thus prepared active ingredient to the reaction zone. The method of the present invention is characterized in that, the active catalyst ingredient can be formed even under a low pressure provided that alcohol or water are excluded, and the reaction can be effected under a low pressure such as in the range of 20~40 atmospheres.

DETAILED DESCRIPTION OF THE INVENTION

In the present invention, as the starting material olefin, unsaturated hydrocarbons having at least one carbon-carbon double bond and 3 or more carbon atoms are applicable; to be concrete, hexane-1, octene-1, octene-3, octadecane-1 and their analogs are useful. Further, olefin mixtures are also applicable as the starting material olefin.

As the starting material alcohol, any alcohol having less than 20 carbon atoms is applicable, and it does not matter whether it is a primary alcohol, secondary alcohol or tertiary alcohol or it is a monohydric alcohol, dihydric alcohol or polyhydric alcohol. To be concrete, methanol, ethanol, 2-ethyl hexanol, ethylene glycol, glycerin, pentaerythritol and their analogs are useful. The ratio of olefin to alcohol or water can be optionally chosen; generally speaking, however, it is desirable to be in the range of 0.2~10 moles of olefin relative to one equivalent of hydroxyl group of alcohol or 1 mole of water.

As the cobalt compound effective as the catalyst, dicobalt octacarbonyl or cobalt carbonyl hydride or a compound forming these derivatives is effective. Examples of such compounds are cobalt octanoate, cobalt stearate, cobalt hydroxide and their analogs. The appropriate ratio of said cobalt compound to water or alcohol is in the range of 0.001~0.1 mole relative to one equivalent of hydroxyl group of alcohol or 1 mole of water. As to the mode of adding the catalyst in the present invention, in order to form an active catalyst ingredient in advance, it is required to put the whole amount of the cobalt compound in the catalyst activation tank together with pyridine base.

For forming this active catalyst ingredient, the presence of said pyridine base is indispensable. The pyridine base herein means mono-, di- and tri-alkyl (having 1~3 carbon atoms)—substituted pyridines, among which pyridines, pyridine, γ-picoline, 3,5-lutidine, 4-ethyl pyridine and their analogs are particularly desirable.

The appropriate amount of these pyridine bases to be added is in the range of 1~100 moles — preferably 3~50 moles — relative to 1 mole of said cobalt compound, but it is not always necessary to add the whole amount of the pyridine base to be employed to the cobalt compound at the time of forming the active catalyst ingredient, that is to say, it will do to add 1~10 moles thereof to the cobalt compound in the reaction zone.

In order to form the active catalyst ingredient by the use of the foregoing proper amount of cobalt compound and pyridine base, it suffices to heat the mixture of said cobalt compound and pyridine base under the pressure of carbon monoxide. On this occasion, the appropriate pressure of carbon monoxide is in the range of 20~200 Kg/cm$^2$, and as long as the pressure of carbon monoxide is in this range, there is no fear of its affecting the activation of catalyst. The temperature for the activation of catalyst is desirable to be in the range of 100°~180°C; when it exceeds 180°C, there are instances where the catalyst activation efficiency lowers, and therefore, it is necessary to maintain a proper temperature. The time for activation suffices to be about 0.5 hour, and any prolongation of this time will be in vain.

As discussed in the foregoing, the present invention is characterized in that it renders it possible to effect the carbonylization reaction under a low pressure such as in the range of 20~40 atmospheres. Accordingly, it has various merits such that it can produce products of high quality, the cost of equipment at the time of industrialization thereof is low, and the safety at the time of operation can be easily maintained. Especially in the case of manufacturing a variety of products in small quantities, like the manufacture of polyhydric alcohols and esters, which requires frequent switchover of apparatuses, the low-pressure method according to the present invention is advantageous from the viewpoint of safety as well as productivity.

Hereunder will be given some comparative examples along with examples of the present invention.

COMPARATIVE EXAMPLE 1

After placing 0.65 mole of decene-1, 0.5 mole of methanol, 0.008 mole of cobalt octanoate and 0.08 mole of γ-picoline in a stainless steel autoclave having a capacity of 300 ml, reaction was effected at a temperature of 160°C for 5 hours while applying a pressure to the extent of 30 Kg/cm$^2$ with carbon monoxide.

After completion of the reaction, the reacted mixture was distilled to separate unreacted olefin, methanol, picoline, etc., but the desired methyl undecanoate was scarcely obtained.

COMPARATIVE EXAMPLE 2

After placing 0.008 mole of cobalt octanoate in a stainless steel autoclave having a capacity of 100 ml, 1 hour's stirring was conducted at a temperature of 160°C while applying first a pressure of 10 Kg/cm$^2$ with hydrogen and then applying a pressure of 150 Kg/cm$^2$ to thereby prepare a catalyst. Meanwhile, after placing 0.65 mole of decene-1, 0.08 mole of γ-picoline and 0.5 mole of methanol in a stainless steel autoclave having a capacity of 300 ml, a pressure of 30 Kg/cm$^2$ was applied thereto with carbon monoxide. Subsequently, the previously prepared catalyst was added to the contents of the latter autoclave, and 5 hours' reaction of the mixture was effected at a temperature of 160°C under the same pressure, or 30 Kg/cm$^2$. The yield rate of methyl undecanoate obtained through distillation of the reacted mixture was 35%.

EXAMPLE 1

After placing 0.008 mole of cobalt octanoate and 0.08 mole of γ-picoline in a stainless steel autoclave having a capacity of 100 ml, 1 hour's stirring was conducted at a temperature of 160°C while applying a pressure to the extent of 50 Kg/cm$^2$ with carbon monoxide to thereby prepare a catalyst. Meanwhile, after placing 0.65 mole of decene-1 and 0.5 mole of methanol in a stainless steel autoclave having a capacity of 300 ml, a pressure of 30 Kg/cm$^2$ was applied thereto with carbon monoxide. Subsequently, the previously prepared catalyst was added to the contents of the latter autoclave, and 5 hours' reaction of the mixture was effected at a temperature of 160°C under the pressure of 30 Kg/cm$^2$. The yield rate of the resulting methyl undecanoate was 80%.

EXAMPLE 2

Reaction was effected by the same operation as in Example 1 except for changing the pressure for the reaction zone from 30 Kg/cm$^2$ to 50 Kg/cm$^2$. The yield rate of the resulting methyl undecanoate was 87%.

EXAMPLE 3

Reaction was effected by the same operation as in Example 1 except for changing the amount of γ-picoline at the time of activation of the catalyst to be 0.04 mole and adding 0.12 mole of γ-picoline to the reaction zone. The yield rate of the resulting methyl undecanoate was 90%.

EXAMPLE 4

After placing 0.016 mole of cobalt octanoate and 0.24 mole of γ-picoline in a stainless steel autoclave having a capacity of 100 ml, 30 minutes' heating was conducted at a temperature of 160°C while applying a pressure to the extent of 50 Kg/cm$^2$ with carbon monoxide to thereby prepare a catalyst. Meanwhile, after placing 0.65 mole of hexene-1 and 0.125 mole of pentaerythritol in a stainless steel autoclave having a capacity of 300 ml, a pressure of 30 Kg/cm$^2$ was applied thereto with carbon monoxide. Subsequently, the previously prepared catalyst was added to the contents of the latter autoclave, and 7 hours' reaction of the mixture was effected at a temperature of 160°C under the pressure of 30 Kg/cm$^2$.

After completion of the reaction, unreacted olefin and γ-picoline were separated from the reacted mixture by distillation, and then fatty acid ester of pentaerythritol was further fractionated by the use of a molecular distillation still.

This ester was composed of 10% of triester and 90% of tetraester.

EXAMPLE 5

Reaction was effected by the same operation as in Example 4 except for substituting 3,5-lutidine for γ-picoline. The thus obtained fatty acid ester of pentaerythritol was composed of 5% of triester and 95% of tetraester.

EXAMPLE 6

Reaction was effected by the same operation as in Example 3 except for substituting water for methanol.

The yield rate of the resulting undecanoic acid was 82%.

EXAMPLE 7

Reaction was effected by the same operation as in Example 6 except for substituting octadecene for decene-1. The yield rate of the resulting nonadecanoic acid was 75%.

What is claimed is:

1. In a process for preparing carboxylic acids or esters by reacting olefin having at least 3 carbon atoms with carbon monoxide and either an alcohol or water, in the presence of cobalt compound and pyridine or a derivative of pyridine, the improvement which comprises the steps of: in a catalyst preparation vessel separate from the reaction vessel, heating materials consisting essentially of cobalt compound and pyridine compound selected from the group consisting of pyridine and mono-, di- and tri-alkyl substituted pyridines, wherein said alkyl has one to three carbon atoms, at a temperature in the range of 100° to 180°C, under a carbon monoxide pressure in the range of 20 to 200 kg/cm$^2$, for a time period of at least about 0.5 hours, effective to prepare a stable complex of said cobalt compound and said pyridine compound as an active catalyst; transferring said active catalyst from said catalyst preparation vessel and adding it to the reaction vessel containing said olefin and either said alcohol or water, as the sole supply of cobalt to said reaction vessel; and then reacting said olefin, either said alcohol or water, and carbon monoxide, in the presence of said active catalyst, until said carboxylic acid or ester is formed.

2. A process according to claim 1, wherein the olefin and the alcohol or water are reacted at a molar ratio of 0.2 to 10 moles of olefin per one equivalent of hydroxyl groups of said alcohol or 1 mole of water.

3. A process according to claim 2, wherein 0.001 to 0.1 mole of said cobalt compound is added per one equivalent of hydroxyl groups of said alcohol or 1 mole of water.

4. A method according to claim 3, wherein said cobalt compound consists of at least one member selected from the group consisting of dicobalt octacarbonyl, cobalt carbonyl hydride or cobalt compound that forms those compounds under the reaction conditions.

5. A process according to claim 3, wherein one to 100 moles of said pyridine compound are added per 1 mole of said cobalt compound.

6. A process according to claim 1 in which the reaction of said olefin, either said alcohol or water, and carbon monoxide is effected by mixing said olefin and either said alcohol or water, and applying a carbon monoxide pressure of 20 to 40 atmospheres.

* * * * *